United States Patent [19]

Franceschini et al.

[11] Patent Number: 4,703,055
[45] Date of Patent: Oct. 27, 1987

[54] BENZAMIDES AND THERAPEUTIC USE THEREOF

[75] Inventors: Jacqueline Franceschini, L'Hay-les-Roses; Renée Gardaix-Luthereau, Cachan; Josette Margarit, Paris, all of France

[73] Assignee: Societe d'Etudes Scientifiques et Industrielles de l'Ile-de-France, Paris, France

[21] Appl. No.: 882,253

[22] Filed: Jul. 7, 1986

[30] Foreign Application Priority Data

Jul. 4, 1985 [FR] France .................. 85 10199

[51] Int. Cl.⁴ ............. C07D 233/54; A61K 31/415
[52] U.S. Cl. ................... 514/400; 548/342; 558/392; 558/275; 260/544 N
[58] Field of Search ............ 548/342; 544/400

[56] References Cited

U.S. PATENT DOCUMENTS 2,376,424  5/1945  Fell ........................ 548/342
4,294,828 10/1981  Thominet et al. ........ 548/342

FOREIGN PATENT DOCUMENTS 1268259  3/1972  United Kingdom ........ 548/342

OTHER PUBLICATIONS

Ried, W., Earl, H. Chem Ber. 115, 475-482 (1982).

Primary Examiner—Henry R. Jiles
Assistant Examiner—Robert C. Whittenbaugh
Attorney, Agent, or Firm—Fitzpatrick, Cella, Harper & Scinto

[57] ABSTRACT

The invention concerns novel benzamides and their pharmacologically acceptable salts which are useful as gastromotor agents and correspond to the following general formula (I):

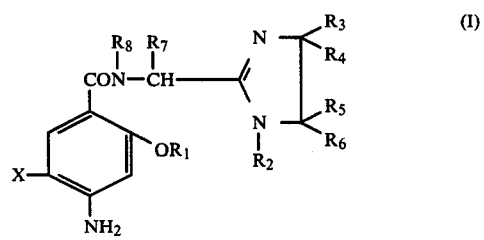

in which:
 $R_1$ is lower alkyl, lower alkenyl or a hydrogen atom;
 $R_2$ is alkyl, lower alkenyl, benzyl, cycloalkylalkyl, cycloalkenylalkyl or a hydrogen atom;
 $R_3$, $R_4$, $R_5$, $R_6$, $R_7$ and $R_8$ each are lower alkyl or a hydrogen atom, and
 X is a halogen atom.

10 Claims, No Drawings

BENZAMIDES AND THERAPEUTIC USE THEREOF

The invention concerns novel benzamide compounds and their pharmacologically acceptable salts, corresponding to the following general formula (I):

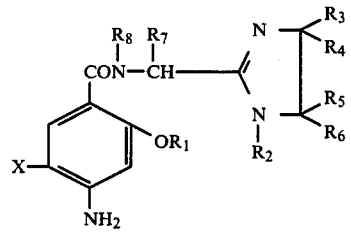

in which:

$R_1$ is lower alkyl, preferably $C_1$–$C_3$ alkyl, such as methyl; lower alkenyl, preferably $C_2$–$C_3$ alkenyl, such as allyl; or a hydrogen atom, $R_2$ is alkyl, preferably $C_1$–$C_3$ alkyl, such as methyl or ethyl; lower alkenyl, preferably $C_2$–$C_3$ alkenyl, such as allyl; benzyl; cycloalkylalkyl, preferably a $C_3$–$C_8$ cycloalkyl - $C_1$–$C_3$ alkyl, such as cyclopropylmethyl; cycloalkenylalkyl, preferably a $C_5$–$C_8$ Cycloalkenyl - $C_1$–$C_3$ alkyl, such as cyclohexenylmethyl; or a hydrogen atom, $R_3$, $R_4$, $R_5$, $R_6$, $R_7$ and $R_8$ are each lower alkyl, preferably $C_1$–$C_3$ alkyl, such as methyl, or a hydrogen atom, and X is a halogen atom, such as chlorine or bromine.

The pharmacologically acceptable salts of the formula I compounds include the non-toxic acid addition salts formed by reacting the benzamides of the invention with the desire acid. The acid may be an inorganic acid, such as sulfuric, sulfamic, nitric, hydrobromic, hydrochloric, phosphoric and the like or an organic acid, such as citric, tartaric, lactic, acetic, succinic, fumaric, maleic, benzoic and the like.

The pharmacologically acceptable salts of the formula 1 compounds also include the non-toxic quaternary ammonium salts of the benzamides of the invention produced by reacting the benzamides with an aliphatic or aromatic alkylating agent, such as methyl chloride, methyl bromide, dimethyl sulfate, methyl p-toluene sulfonate and the like. In addition, the novel benzamide compounds include the N-oxides formed by utilizing the conventional oxidizing agents; see, for example, U.S. Pat. No. 3,839,330, issued Oct. 1, 1974.

The dextrorotatory and levorotatory isomers of the foregoing compounds of the invention are also included within the scope of this invention. Such optically active compounds are conventionally resolved employing a suitably selected optically active acid, which is added to the racemate. The salts thus obtained are separated, for example, by making use of their differences in solubility in an appropriate solvent or by other conventional techniques. Typically, D- or L-dibenzoyl-tartaric acid is employed to resolve the racemate.

The compounds of the invention exhibit a remarkable gastromotor effect.

The inventive compounds are also remarkable in that, to a large extent, they spare the central dopaminergic receptors and cause little or no neurological disturbances, which can occur with other methoxybenzamides.

The compounds according to the present invention may be prepared by reacting an acid having the following general formula (II):

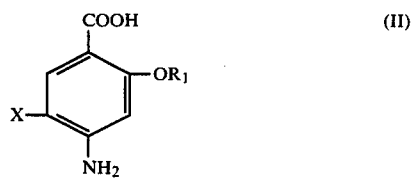

in which $R_1$ and X have the same meaning as set forth above, with a nitrile having the following formula (III):

to produce a substituted cyanomethylbenzamide derivative having the following general formula (IV):

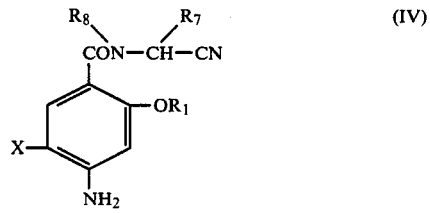

which will react with a substituted diamine to give the expected compound of formula (I).

In accordance with an alternative form of that synthesis procedure, it is possible to prepare from an acid having the formula (II), a reactive derivative of that acid such as, for example, a mixed ester having the following general formula (V):

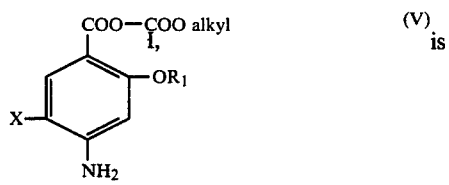

or an acid chloride having the following general formula (VI):

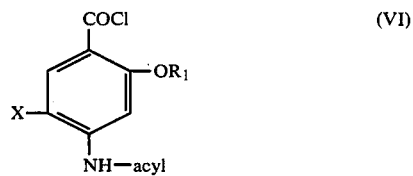

in which the values of $R_1$ and X are the same as defined hereinbefore, which will react with a nitrile of formula (III) to give the cyanomethylbenzamide derivative of formula (IV) and finally the expected compound of formula (I).

Some of the synthesis intermediates are novel compounds, in particular the nitriles of formula (IV) and the mixed esters of formula (V).

In order to illustrate the invention, illustrative example thereof will be described below. Such examples do not constitute a limitation of the scope of the invention. All temperatures are in ° C. unless otherwise indicated.

EXAMPLE I:

N-[(1-ETHYL 2-IMIDAZOLIN-2-YL)METHYL] 2-METHOXY 4-AMINO 5-CHLORO BENZAMIDE

Step 1: N-(CYANOMETHYL) 2-METHOXY 4-AMINO 5-CHLORO BENZAMIDE into a three liter balloon flask provided with a sealed agitator, a reflux condenser, a thermometer and a dropping funnel, there were introduced 100 g of 2-methoxy 4-amino 5-chlorobenzoic acid (0.5 mole ), 655 cc of chloroform which was dried over $CaCl_2$ and 51 g of triethylamine which was dried over potash (0.5 mole). After the acid was dissolved, a salt was immediately precipitated. The resulting suspension was cooled to from 0° to 5° C. and 54 g of ethyl chloroformate (0.5 mole) was poured in dropwise. The precipitate dissolved as the pouring operation proceeded and, at the end of the addition operation, a solution was formed which was then further agitated for 1 hour at 0° C.

A solution of 51 g of aminoacetonitrile hydrochloride (0.5 mole +10% excess) in 150 cc of chloroform and 56 g of triethylamine which was dried over potash (0.5 mole +10% excess) was then added dropwise, with the temperature being maintained at between 5° and 10°; and a precipitate formed.

When the addition operation was concluded, agitation was effected for a further hour at 10°. The major part of the chloroform was then removed, the residue was dissolved in water and was rendered alkaline by the additin of 30% soda lye. The remaining precipitate was drained, washed with water until the washing waters were neutral, and dried at 40° C. in a ventilated oven.

Weight obtained=106 g
MP=196° C.
Yield=88.5%

Step 2: N-[1-ETHYL 2-IMIDAZOLIN-2-YL) METHYL] 2-METHOXY 4-AMINO 5-CHLOROBENZAMIDE Into a 250 cc balloon flask provided with a sealed agitator, a reflux condenser and a thermometer, there were introduced 26 g of N-(cyanomethyl ) 2-methoxy 4-amino 5-chlorobenzamide (0.109 mole), 19 g of N-ethyl ethylenediamine (2×0.109 mole) and 5 drops of carbon disulphide. A thick slurry was obtained, which was difficult to agitate and which was heated on an oil bath. A solution was obtained at a temperature of 110° C., and ammonia gas was evolved. Heating was continued to a temperature of 120° to 130°. After 12 minutes, gases ceased to be evolved.

The oil bath was then removed and cooling was effected with agitation to about 40°. Then, 200 cc of ice water was added. The precipitate which was formed was drained, washed with water and dried at 40° in a ventilated oven.

Weight obtained=25 g
Yield=74%

The product obtained contained some starting nitrile. The product was redissolved in water and acetic acid. The insoluble matter was filtered off and the solution was rendered alkaline by the addition of 30% soda lye until a phenolphthalein color change occured. The product which precipitated was drained, washed with water until the washing waters were neutral and dried at 40° C.

Weight obtained=20 g
Purification yield=80%

The compound was obtained in the form of white crystals which were soluble in dilute acetic acid, and were highly soluble in chloroform (MP =175°-176° Büchi).

EXAMPLE II:

N-[(1-ALLYL 2-IMIDAZOLIN-2-YL) METHYL] 2-METHOXY 4-AMINO 5-CHLOROBENZAMIDE

Into a 500 cc balloon flask provided with a sealed agitator, a reflux condenser on which was mounted a bubble counter containg vaseline oil, a thermometer and a dropping funnel, there was introduced 54 g of N-(cyanomethyl) 2-methoxy 4-amino 5-chlorbenzamide in finely powdered form, and 45 g of N-allyl ethylenediamine. A very thick slurry was obtained which was difficult to agitate and which was heated at a temperature of 100° by means of an oil bath. Then, 15 drops of carbon disulphide were added to the slurry. It was observed that the temperature rose rapidly to 110° and that a very substantial amount of gas was evolved. At the same time the slurry slowly dissolved. After 10 minutes, the speed at which the gas was evolved decreased. A further amount of 12 drops of carbon disulphide was added. Ammonia began to be evolved again, the initial product was dissolved entirely and then a product crystallized. The reaction temperature rose to 135°. Five minutes later, gas ceased to be given off. Cooling was immediately effected to about 15° to 20° C. and the reaction mixture was dissolved in 1 liter of water. The resulting product was drained, washed with copious amounts of water and dried at 40° in a ventilated oven.

Weight obtained=63 g
Yield=87%

The above-indicated 63 g of product was redissolved hot in 126 cc of 2-methoxy ethanol. The boiling solution was filtered with carbon black and then cooled. The base which recrystallized out was drained, washed with 2-methoxy ethanol and dried at 40°.

Weight obtained=46.5 g
MP=177°-178° C.
Yield=74% Total yield=64%

EXAMPLE III

N-[(1-BENZYL 2-IMIDAZOLIN-2-YL) METHYL] 2-METHOXY 4-AMINO 5-CHLOROBENZAMIDE HYDROCHLORIDE

Step 1: N-[(1-BENZYL 2-IMIDAZOLIN-2-YL) METHYL] 2-METHOXY 4-AMINO 5-CHLOROBENZAMIDE 81.5 g of N-(cyanomethyl) 2-methoxy 4-amino 5-chlorobenzamide and 102 g of N-benzyl ethylenediamine were introduced into a 500 cc balloon flask provided with a sealed agitator, a reflux condenser upon which was mounted a bubble counter containing vaseline oil, a thermometer and a dropping funnel. The mixture was heated to 105°. Then, 15 drops of carbon disulphide were introduced. The initial suspension was rapidly solubilized. The temperature rose to 125° and, at the same time, a substantial amount of gas was evolved.

After 10 minutes, with the rate at which gas was evolving, decreasing, an additional 15 drops of carbon disulphide was added. Gas again began to be evolved at once, the reaction temperature rose to 129° and the mixture entirely dissolved. When the gas ceased to be evolved, the reaction was stopped and cooling was effected. The substance which crystallized out was immediately dissolved in 500 cc of ether, drained, washed with ether, dried in the air and then at 40°.

Weight obtained = 125 g
Yield = 98%

125 g of product were recrystallized from 125 cc of 2-methoxy ethanol.

Weight obtained = 84 g
Crystallization yield = 67%

The 84 g of product was redissolved in water and sufficient acetic acid to adjust the pH value to 4. The solution obtained was filtered with carbon black and then made alkaline by the addition of 20% ammonia until phenolphthalein indicator turned color. The product which precipitated was drained, washed with water until the washing waters were neutral, and dried at 40°.

Weight obtained = 61 g
Purification yield = 73%
MP = 165°–166°

The product obtained was still coloured and still contained a slight amount of impurity. It was recrystallized again from 61 cc of 2-ethoxy ethanol. After draining, it was washed with iced 2-ethoxy ethanol and then with water to remove any trace of solvent, and then dried at 40°.

Weight obtained = 57.5 g
Crystallization yield = 94%
Purification operations yield = 46%
Total yield = 45%

Step 2: N-[(1-BENZYL 2-IMIDAZOLIN-2-YL) METHYL] 2-METHOXY 4-AMINO 5-CHLOROBENZAMIDE HYDROCHLORIDE 57.5 g of base was dissolved hot in 230 cc of absolute ethanol and a solution of 5.7 g of hydrogen chloride gas in 15 cc of ethanol was added until Congo red indicator changed color.

The solution obtained was then cooled and the hydrochloride salt formed crystallized out slowly.

The salt was drained after several hours, washed with absolute ethanol and dried at 40°.

Weight obtained:
1st stream = 60 g Mol. wt. (AgNO$_3$N/10) = 413 2nd stream = 3 g
Total weight obtained = 63 g (Yield = 100%)

The 63 g of hydrochloride salt was recrystallized from 190 cc of absolute ethanol.

Weight obtained = 54 g
Recrystallization yield = 86%

The hydrochloride obtained retains traces of ethanol which remained even after prolonged drying under vacuum at 45° and then 70°.

Finally, the product was rapidly dissolved in water, drained and dried.

Weight obtained = 40 g
Mol. wt. (AgNO$_3$N/10) = 410.5
MP = 258° C.
Purification yield = 74%
Total yield: 63%

EXAMPLE IV

N-[(1-CYCLOPROPYLMETHYL 2-IMIDAZOLIN-2-YL) METHYL] 2-METHOXY 4-AMINO 5-CHLOROBENZAMIDE)

45 g of N-(cyanomethyl) 2-methoxy 4-amino 5-chlorobenzamide in finely powdered form and 43 g of N-cyclopropylmethyl ethylene diamine were introduced into a 500 cc balloon flask provided with a sealed agitator, a reflux condenser upon which was mounted a bubble counter containing vaseline oil, a thermometer and a dropping funnel. A thick slurry was obtained which was heated employing an oil bath at 110°. Then, 20 drops of carbon disulphide were gradually added. A substantial amount of ammonia was immediately observed to be evolved, with a rapid rise in temperature to 120°. At the same time the medium became fluid and was completely dissolved after 6 minutes.

Shortly afterwards, the product formed, crystallized out. The temperature of the mix fell and the rate at which gas was evolved decreased markedly, before stopping completely.

After cooling the precipitate was dissolved in ether. The product recrystallized. Thereafter, it was drained, washed with ether and dried in the air and then at 50°.

Weight obtained = 64 g
Yield = 100%

The 64 g of recovered product was redissolved hot in 225 cc of absolute ethanol. The boiling solution was filtered with carbon black and then cooled. The base which then rapidly crystallized was drained, washed with ethanol and then with ether, and dried in the air and then at 50°.

Weight obtained = 29 g
MP = 184° C.
Recrystallization yield = 45.5%

A second recovery procedure made it possible to recover an additional 11 g of product which was immediately recrystallized from 33 cc of absolute ethanol.

Weight obtained = 7 g
Total weight obtained = 36 g
Total recrystallization yield = 56%

The 36 g of base was recrystallized from 125 cc of absolute ethanol and then the resulting 29 g of product obtained was recrystallized from 145 cc of isopropanol.

Weight obtained = 27.5 g
MP = 182.5°–184.5° C.
Recrystallization yield = 76.5%
Total yield = 43%

EXAMPLE V

N-[(1-ETHYL 2-IMIDAZOLIN-2-YL) METHYL]2-ALLYLOXY 4-AMINO 5-CHLOROBENZAMIDE

Step 1: ETHYL 2-HYDROXY 4-ACETAMINO 5-CHLOROBENZOATE 258 g of ethyl 2-hydroxy 4-acetamino benzoate and 1150 cc of acetic acid were introduced into a 3 liter balloon flask provided with a sealed agitator, a reflux condenser and a thermometer. The mixture was heated on a water bath at 40° until it dissolved. 153.5 g of N-chlorosuccinimide was then added and heated at 40° to 50° C. until total dissolution occurred. The solution obtained was then left in a drying oven at 50° C. for 48 hours.

A crystallized product resulted which was dissolved in 8 liters of water. The crystals were drained, washed abundantly with water until the washing waters were neutral, and dried at 40° C. in a ventilated oven.

Weight obtained = 266 g
MP = 150° C.
Yield = 89%

The 266 g of product were recrystallized from 300 cc of acetic acid.
Weight obtained = 198 g
MP = 159° C.
Recrystallization yield = 74.5%
Total yield = 66%

Step 2: ETHYL 2-ALLYLOXY 4-ACETAMINO 5-CHLOROBENZOATE 53 g of potassium carbonate in powdered form, 5.5 g of benzyl tributylammonium chloride, 220 cc of acetonitrile and 46.5 g of allyl bromide, and 99 g of ethyl 2-hydroxy 4-acetamino 5-chlorobenzoate, were introduced into a one liter balloon flask provided with a sealed agitator, a reflux condenser and a thermometer. The suspension obtained was heated under reflux for 3 hours 30 minutes until a test sample of clear solution diluted in a little alcohol did not color in the presence of ferric chloride. A portion of the acetonitrile product was then distilled and the residue was dissolved in water. The mineral salts dissolved. The allyloxy ester intermediate which precipitated was drained, washed with water until the bromine ions were eliminated and then the ester was dried at 35° in a ventilated oven.
Weight obtained = 130 g
Theoretical amount = 114 g
The product obtained was half-crystallized. It was dissolved in 260 cc of 60% boiling ethanol. The solution obtained was then filtered with carbon black and cooled. The ester intermediate which recrystallized was drained, washed with 60% ethanol and dried in a ventilated oven at 40°.
Weight obtained = 70.5 g
MP = 80° C.
Recrystallization yield = 62%
Total yield = 62%

Step 3: 2-ALLYLOXY 4-AMINO 5-CHLOROBENZOIC ACID 68 g of ethyl 2-allyloxy 4-acetamino 5-chlorobenzoate, 172 cc of ethanol and 50.5 cc of 30% soda lye were introduced into a one liter balloon flask provided with a reflux condenser, and heating was effected under reflux on a water bath for a period of 3 hours. The solution obtained was then dissolved in 2 liters of water and filtered with carbon black in order to remove cloudiness and then acidified by the addition of 45 cc of concentrated hydrochloric acid (until Congo red indicator turned color). The acid which precipitated was drained after cooling, washed with water until the washing waters were neutral and dried at 50°.
Weight obtained = 50 g
Mol. wt. (KOH N/10-potentiometry) = 232
MP = 142°C.
Yield = 95%

Step 4: N-(CYANOMETHYL 2-ALLYLOXY 4-AMINO 5-CHLORO BENZAMIDE 51 g of 2-allyloxy 4-amino 5-chlorobenzoic acid, 220 cc of chloroform and 23 g of triethylamine were introduced into a 500 cc ballon flask provided with a sealed agitator, a reflux condenser, a thermometer and a dropping funnel. The solution obtained was cooled to 0° C. and a triethylammonium salt crystallized out. 24.5 g of ethyl chloroformate was then added dropwise to that soluiton, with the temperature being maintained at between 0° and 5° by cooling in an ice bath. The precipitate gradually dissolved and a solution was obtained which was agitated for a futher period of 30 minutes.

A solution of 21 g of aminoacetonitrile hydrochloride in 220 cc of chloroform and 23 g of triethylamine were then added. The reaction temperature rose to 32°. When the addition had been completed, agitaion was continued for a further period of 1 hour. The major part of the chloroform was then removed and the residue was dissoled in water. The product obtained was drained, washed with water, with dilute soda, then again with water, and finally dried at 40° in a ventilated oven.
Weight obtained = 49.5 g
MP = 149° C.
Yield = 83%

Step 5: N-[(1-ETHYL 2-IMIDAZOLIN-2-YL) METHYL]2-ALLYLOXY 4-AMINO 5-CHLOROBENZAMIDE 49 g of N-(cyanomethyl) 2-allyloxy 4-amino 5-chlorobenzamide and 32.5 g of N-ethyl ethylenediamine were introduced into a 500 cc balloon flask provided with a sealed agitator, a reflux condenser on which was disposed a bubble counting tube containing vaseline oil, a thermometer and a dropping funnel. Heating of the contents was effected to 120° by means of an oil bath which had been pre-heated to 120° C. The reactants were solubilized. 10 drops of carbon disulphide were then added. Whitish vapours were immediately observed to form within the balloon flask, and gas was seen to be evolved.

Heating at 120° was continued until gas ceased to be evolved; namely for a period of 1 hour 30 minutes. Cooling to 40° was then effected, followed by the addition of chloroform. The chloroform solution obtained was washed with water so as to remove the excess amine. The solution was then dried over sodium sulphate. The chloroform was evaporated under a slight vacuum and the residue was dissolved with ethyl acetate. The substance which crystallized out was drained, washed with ethyl acetate and dried at 40°.
Weight obtained = 39 g
Yield = 63%

The 39 g of product was redissolved hot in 75 cc of methyl ethyl ketone. The boiling solution was filtered with carbon black and then cooled. The base which crystallized out was drained, washed with methyl ethyl ketone and dried at 40°.
Weight obtained = 31
Recrystallization yield = 80%

The 31 g of base product was recrystallized from 65 cc of isopropanol. After draining, the recrystallized substance was washed with isopropanol and then with ether. The product was then dried in the air and then at 40°.
Weight obtained = 27 g
MP = 136.5°-137.5° C.
Recrystallization yield = 87%
Recrystallization operations yield = 70%
Total yield = 44%

EXAMPLE VI:

N-[(1-ETHYL 2-IMIDAZOLIN-2-YL) METHYL]2-METHOXY 4-AMINO 5-BROMOBENZAMIDE

Step 1: N-(CYANOMETHYL) 2-METHOXY 4-AMINO 5-BROMOBENZAMIDE 107 g of 2-methoxy 4-amino 5-bromobenzoic acid in finely divided form, 531 cc of chloroform and 44 g of triethylamine were introduced into a two liter balloon flask provided with a sealed agitator, a reflux condenser, a thermometer and a dropping funnel and then heated until dissolution occurred. Cooling to 0° was then effected. Thereafter, 47 g of ethyl chloroformate was poured dropwise into the resulting solution, with the temperature being maintained at between 0° and 5° by cooling. When the addition operation was concluded, agitation was effected for a further hour at between 0° and 5°.

At the same time, 44 g of aminoacetonitrile hydrochloride and 531 cc of chloroform were introduced into a one liter balloon flask provided with an agitator and, after cooling to 0°, 48 g of triethylamine was added. A very fine precipitate was then formed. The contents of the balloon flask were gradually added to the chloroform solution of mixed anhydride which had been produced previously, with the temperature being maintained at between 0° 5°. When the introduction operation was concluded, agitation was effected for a further period of 1 hour at between 0° and 5° and then the temperature was permitted to rise.

A grey, gelatinous precipitate formed which was suspended in the chloroform. One (1) liter of water was added and all the chloroform was removed by being entrained in water and distilled off.

Cooling was then effected, followed by the addition of 10 cc of 10% soda lye so as to redissolve traces of unreacted acid. The remaining product was the drained, washed with water until the Cl⁻ ions were removed and dried at 50°.

Weight obtained = 117 g
MP = 200° C.
Yield = 95%

The poduct was suspended in one liter of water and 10 cc of 10% soda lye. Then, the product was drained, washed with water until the washing waters were neutral and dried at 50°.

Weight obtained = 108 g
MP = 206° C.
Purification yield = 92%
Total Yield = 88%

Step 2: N-[(1-ETHYL 2-IMIDAZOLIN-2-YL) METHYL]2-METHOXY 4-AMINO 5-BROMOBENZAMIDE 85 g of N-(cyanomethyl) 2-methoxy 4-amino 5-bromobenzamide is finely divided form and 53 g of N-ethyl ethylenediamine were introduced into a 500 cc balloon flask provided with a sealed agitator, a reflux condenser on which was disposed a bubble counter containing vaseline oil, a thermometer and a dropping funnel. The thick suspension obtained was heated employing an oil bath to a temperature of 105°. 20 drops of carbon disulphide were then added. A reaction began immediately, with ammonia being evolved. The medium became fluid and rapidly changed into a thick liquid. Shortly afterwards, the product formed crystallized out. The product was cooled immediately, and dissolved with ether. The product obtained was drained, washed with ether and dried in the air.

Weight obtained = 102 g
Yield = 96%

The 102 g of product obtained was redissolved in 200 cc of chloroform. A small amount of insoluble matter remained, which was filtered under vacuum. The chloroform was then totally removed. The residue which crystallized out was immediately redissolved in 153 cc of boiling ethanol. The solution obtained was cooled to about 10°.

The product which crystallized out again was drained, washed with iced ethanol and then with ether, dried in the ai and then at 50° and finally under vacuum at 50°.

| Weight obtained: | 1st stream | = 43 g | MP = 178° C. |
|---|---|---|---|
| | 2nd stream | = 24 g | MP = 178° C. |
| Total weight obtained | | = 67 g | |

Mol. wt. (ClO₄H N/10) = 355.5
MP = 176.5°-178.5° C.
Recrystallization yield = 66%
Total yield = 63%

EXAMPLE VII:

N-METHYL N-[(1-ETHYL 2-IMIDAZOLIN-2-YL) METHYL]2-METHOXY 4-AMINO 5-CHLOROBENZAMIDE METHANE SULPHONATE

Step 1: N-METHYL N-(CYANOMETHYL) 2METHOXY 4-AMINO 5CHLOROBENZAMIDE 101 g of 2-methoxy 4-amino 5-chlorobenzoic acid, 250 cc of chloroform and 50.5 g of triethylamine were introduced into a two liter balloon flask provided with a sealed agitator, a reflux condenser, a thermometer and a dropping funnel, and heating of the mixture was effected until dissoluiton occurred, followed by cooling the mix to 0°. A triethylammonium salt formed and then crystallized. 54.5 g of ethyl chloroformate was then poured dropwise into the resulting mix, with the temperature being maintained at between 0° and 5° to form a mixed anhydride. When the addition operation was concluded, agitation was effected for a further period of 30 minutes at 5° C.

At the same time, 400 cc of chloroform and 55.5 g of triethylamine were introduced into a one liter balloon flask provided with an agitator and the mixture was cooled in an ice bath. 59 g of methylamino acetonitrile hydrochloride in finely divided form was then added gradually. The solution thus obtained was then gradually added to the solution of mixed anhydride which was produced previously, with the temperature being maintained at between 5° and 10°. At the end of the addition operation, agitation was effected for a further period of 1 hour at 5°C. The temperature of the reaction mix was permitted to rise and the reaction medium was left overnight.

The chloroform was then distilled off under a slight vacuum. The residue was dissolved in water and the last traces of chloroform were removed by entrainment with water. The remaining product crystallized out.

A few drops of soda lye were then added to make the medium slightly alkaline and then the product obtained was drained, washed with water until the Cl⁻ ions were removed, and dried at 40°.

Weight obtained = 92 g
MP = 128° C.
Yield = 72.5%

Step 2: N-METHYL N-[(1-ETHYL 2-IMIDAZOLIN-2-YL) METHYL]2-METHOXY 4-AMINO 5-CHLOROBENZAMIDE 50 g of N-methyl N-(cyanomethyl) 2methoxy 4-amino 5-chloro benzamide in finely divided form was introduced into a 250 cc balloon flask provided with a sealed agitator, a reflux condenser, a thermometer and a dropping funnel. The contents were heated to about 80° C. 35 g of N-ethyl ethylenediamine was added and the solution obtained was heated to 120°. 5 drops of carbon disulphide were then added and heating was maintained for about 2 hours at between 125° and 130° until ammonia ceased to be evolved. The solution was then dissolved in ice water and acidified with acetic acid. The solution was immediately filtered with carbon black and then made alkaline under cooling, using a substantial excess of 30% soda lye. The oil which separated out was left to settle and extracted three times with chloroform. The chloroform solution was then washed twice with water and then dried over sodium sulphate. The chloroform was then distilled off, under vacuum, until a constant weight of product was attained.

Weight obtained = 73 g
Theoretical amount = 64 g

The product obtained contained 25% of chloroform; representing 55 g of useable product; namely, a yield of 86%.

Purification 129 g of product (corresponding to 96 g of pure base) was dissolved hot in 200 cc of ethanol and 26 g of oxalic acid. After cooling, the oxalate salt precipitated in the form of a gelatinous mass, which then solidified. The product obtained was drained, washed with ethanol and dried at 40°.

Weight obtained = 110 g
Yield = 91.5%

The 110 g of oxalate salt obtained was dissolved in 1 liter of water. An insoluble material remained, which was filtered with carbon black. The solution obtained was then made alkaline with external cooling in an ice bath by the addition of 150 cc of 30% soda lye.

The oil, which separated out was permitted to settle and was then extracted with chloroform. The chloroform solution was washed twice with water and then dried over sodium phosphate. The chloroform was then distilled off under vacuum until a constant weight of product was attained. Weight obtained = 93 g The product obtained still contained 19 to 20% of chloroform, giving a true weight of base of 75 g. Purification yield = 78%

Step 3: N-METHYL N-[(1-ETHYL 2-IMIDAZOLIN-2-YL) METHYL]2-METHOXY 4-AMINO 5-CHLOROBENZAMIDE METHANE SULFONATE 93 g of product (corresponding to 75 g of pure base) was dissolved in 220 cc of isopropanol and 22.5 g of methane sulphonic acid. Crystallization was induced by seeding. The product methane sulphonic salt formed, slowly crystallized; was left overnight and then drained; was washed with isopropanol and then dried at 40°.

Weight obtained = 74 g
Yield = 76%

The 74 g of methane sulphonte salt was recrystallized from 185 cc of isopropanol. After draining, washing and drying, the product was recovered as follows:

Weight obtained = 70 g
Recrystallization yield = 95%

The product, which was obtained, retained isopropanol which was not removed by prolonged drying at 40° under a reduced pressure. The product was, accordingly, redissolved in 45 cc of water. The solution was transferred to a large crystallizing dish and dried initially in the air and then in a ventilated oven at 20° in order to evaporate the maximum amount of water. The residual product was then dried thoroughly at 40°.

Weight obtained = 67 g
Mol. Wt. (Cl⁻ after mineralization) = 421
MP = 163.5°-164° C.
Purification yield = 96%
Yield of the purification operations = 91%
Total yield of the reaction = 69%

EXAMPLE VIII:

N-[(1-METHYL 2-IMIDAZOLIN-2-YL)METHYL]2-METHOXY 4-AMINO 5-CHLOROBENZAMIDE HYDROCHLORIDE

Step 1: N-[(1-METHYL 2-IMIDAZOLIN-2-YL) METHYL]2-METHOXY 4-AMINO 5-CHLOROBENZAMIDE 48 g of N-(cyanomethyl) 2-methoxy 4-amino 5-chlorobenzamide and 30 g of N-methyl ethylene diamine were introduced into a 250 cc balloon flask provided with a sealed agitator, a reflux condenser upon which there was disposed a bubble counter containing vaseline oil, a thermometer and a dropping funnel.

The suspension obtained was heated at 105° in an oil bath and 15 drops of carbon disulphide were then added. Ammonia immediately was evolved and the initial suspension dissoled. Heating at 105° was maintained until the gas ceased to be evolved (a period of 25 minutes) and the solution was cooled. The product which began to crystallize was then dissolved in ether, drained, washed with ether and then ethanol, and dried.

Weight obtained = 45 g
MP = 228° C.
Yield = 76%

The 45 g of product was recrystallized from 180 cc of 2-methoxy ethanol. The product which recrystallized out, upon cooling, was drained, washed with 2-methoxy ethanol and dried at 50°.

Weight obtained = 36.5 g
Mol. wt. (HClO₄N/10-potentiometry) = 229
MP (Büchi) = 216°-219° C.
Recrystallization yield = 81%

Step 2: N-[(1-METHYL 2-IMIDAZOLIN-2-YL)METHYL]2-METHOXY 4-AMINO 5CHLOROBENZAMIDE HYDROCHLORIDE A solution of 5.5 g of hydrogen chloride gas in 8 cc of absolute ethanol was added to 45 g of base product in finely divided form in suspension in 90 cc of ethanol. After the base dissolved, a hydrochloride formed and crystallized out. The hydrochloride was drained, washed with absolute ethanol, dried at 50° C. and then under vacuum at 40° C. to remove any trace of solvent.

Weight obtained = 43 g
Mol. wt. (AgNO$_3$ N/10) = 344 ⎫ Corresponding to a product
H$_2$O (Fischer) = 3% ⎬ containing about ½ mole of water
MP = 207.5°–210° C.
Yield of hydrated product = 84%

EXAMPLE IX:

N-[(1-ETHYL 4-METHYL 2-IMIDAZOLIN-2-YL METHYL]2-METHOXY 4-AMINO 5-CHLOROBENZAMIDE 35 g of N-(cyanomethyl) 2-methoxy 4-amino 5-chlorobenzamide and 26 g of 1-ethylamino 2-aminopropane, which was previously dried, were introduced into a 250 cc balloon flask provided with a sealed agitator, a reflux condenser on which there was disposed a bubble counter containing vaseline oil, a thermometer and a dropping funnel. The solution obtained was heated to around 130° C. 10 drops of carbon disulphide were then added. A substantial amount of ammonia was immediately evolved and at the same time the medium solubilized.

After 45 minutes, the gas ceased to be evolved and the initial suspension changed into a thick chestnut-colored solution in which a precipitate then appeared. The reaction medium was then left to cool down to 30° C. and was thereafter dissolved in ether.

The product obtained was drained, washed with ether and dried in the air.
Theoretical amount = 47 g
Weight obtained = 49 g The N.M.R. spectrum indicates the presence of impurities (inter alia-diamide) and about 70% of the expected compound.

The 49 g of product was dissolved in 15 cc of boiling 2-ethoxy ethanol. The solution obtained was filtered with carbon black. The product recrystallized out very quickly. It was drained, washed with 2-ethoxy ethanol and then with ether, dried in the air and then at 40°.
Weight obtained = 25 g
Recrystallization yield = 51%

The 25 g of product was recrystallized from 60 cc of 2-ethoxy ethanol. The product obtained after draining, washing and drying was crystallized from 26 cc of 2-ethoxy ethanol.
Weight obtained = 10 g
MP = 219°–221° C.
Recrystallization yield = 40%
Yield of the recrystallization operations = 20.5%
Total yield = 20.5%

EXAMPLE X:

N-[(2-IMIDAZOLIN-2-YL) METHYL]2-METHOXY 4-AMINO 5-CHLOROBENZAMIDE NITRATE

Step 1: N-[(2-IMIDAZOLIN-2-YL)2-METHOXY 4-AMINO 5-CHLOROBENZAMIDE 120 g of N-(cyanomethyl) 2-methoxy 4-amino 5-chlorobenzamide and 60 g of ethylene diamine were introduced into a 500 cc balloon flask provided with a sealed agitator, a reflux condenser on which there was disposed a bubble counter containing vaseline oil, and a thermometer. The thick suspension thus obtained was heated employing an oil bath.

After heating for 15 minutes, the temperature of the bath was measured at 140° C. Gas was then observed to be evolved in the flask and the rate at which the gas was evolved increased rapidly. At the same time, the reaction contents solubilized to finally yield a dark-brown solution. The reaction mixture was maintained at 140° for 1 hour until gas ceased to be evolved.

After cooling, the mixture was dissolved in dry chloroform and agitated for 30 minutes. The product which crystallized out was drained, washed with chloroform and dried in the air and then in an oven.
Weight obtained = 135 g
Yield = 95%

Step 2: N-[(2-IMIDAZOLIN-2-YL) METHYL]2-METHOXY 4-AMINO 5-CHLOROBENZAMIDE NITRATE 80 g of base in finely divided form was suspended in 120 cc of water. Then, 27.5 cc of nitric acid (d=1.33) was added in a single portion. The base dissolved and a nitrate salt crystallized. The salt was cooled, drained, washed with iced water until the washing waters were neutral and dried at 50°.
Weight obtained = 35.5 g
Yield = 36%

The 35.5 g of product was redissolved hot in 175 cc of 2-methoxy ethanol. The boiling solution was filtered with carbon black. Recrystallization was effected very quickly. After cooling, the recrystallized product was drained, washed with 2-methoxy ethanol and dried at 40.

Weight obtained = 26 g
Recrystallization yield = 73%

The 26 g of product was recrystallized from 180 cc of 2-methoxy ethanol. Recrystallization was effected very quickly. After cooling, draining and drying, a product was recovered as follows:
Weight obtained = 21 g
Recrystallization yield = 81%

The 21 g of product was recrystallized from 125 cc of 2-methoxy ethanol.
Weight obtained = 18 g
Recrystallization yield = 85%
Mol. wt. (HCLO$_4$N/10) = 351.5
MP = 229°–232° C.
Yield of the recrystallization operations = 50%
Total yield = 18%

The N.M.R. spectrum of the product was compatible with the structure expected.

EXAMPLE XI:

N-[(1-ETHYL 4-DIMETHYL 2-IMIDAZOLIN-2-YL)METHYL]2-METHOXY 4-AMINO 5-CHLOROBENZAMIDE 78 g of n-(cyanomethyl) 2-methoxy 4-amino 5-chloro benzamide, 79 g of (2-amino 2-methylpropyl)ethylamine and 5 drops of carbon disulphide were introduced into a 500 cc balloon flask provided with a sealed agitator, a reflux condenser on which there was disposed a bubble counter containing vaseline oil, a thermometer and a dropping funnel. The suspension obtained was heated using an oil bath at a temperature of 130°.

5 additional drops of carbon disulphide were added. The suspension solubilized slightly and ammonia was evolved slowly. Heating at 130° was maintained for a period of 6 hours 30 minutes until thick clear solution was obtained. The solution was then cooled and dissolved in 320 cc of chloroform. A portion of the solution was solubilized in the chloroform, while the other part crystallized out. The crystals were drained, washed with chloroform and dried. 21 g of the starting nitrile product were recovered.

The chloroform solution was filtered with carbon black and concentrated under vacuum until a constant weight was attained. The residual oil was then dissolved with ether and crystallized. The crystals were drained, washed with ether and dried in the air.

Weight obtained=52 g
Yield=47%
Yield with respect to the nitrile=64%

A dark beige product was recrystallized from 150 cc of methyl ethyl ketone.

Weight obtained=23 g
Recrystallization yield=44%

The 23 g of product was recrystallized from 92 cc of methyl ethyl ketone.

Weight obtained=20.5 g
Recrystallization yield=89%

The 20.5 g of product was redissolved hot in 205 cc of methylene chloride and the solution obtained was filtered hot with carbon black. 90 cc of methylene chloride were then distilled off under a slight vacuum and the remaining solution was cooled. The product which recrystallized out was drained, washed with ether, dried in the air and then at 40°.

Weight obtained=16 g
Mol. wt. (HClO$_4$N/10 -potentiometry)=337
Recrystallization yield=77%
MP=185°–186° C.
Yield of the recrystallization operations=30%
Total yield=14%

EXAMPLE XII:

N-[(1-ETHYL 2-IMIDAZOLIN-2-YL)METHYL]2-HYDROXY 4-AMINO 5-CHLOROBENZAMIDE HYDROCHLORIDE

Step 1: 2-ACETOXY 4-ACETAMINO 5-CHLOROBENZOYL CHLORIDE 501 g of thionyl chloride and 71.5 g of 2-acetoxy 4-acetamino 5-chlorobenzoic acid were introduced into a two liter balloon flask provided with a reflux condenser. Heating was effected by a water bath under reflux until dissolution of reactants occurred. Some cooling was applied and 71.5 g of 2-acetoxy 4-acetamino 5chlorobenzoic acid was added. Heating was effected as before under reflux for a period of 1 hour, but without causing the acid to dissolve. 63 g of thionyl chloride was added. The acid dissolved immediately, and an acid chloride quickly crystallized.

A part of the thionyl chloride was distilled off under vacuum and the crystallized residue was dissolved with petroleum ether. The acid chloride obtained was drained and washed quickly with petroleum ether and dried under vacuum over P$_2$O$_5$.

Weight obtained=143 g
Mol. wt. (Cl$^-$ after mineralization)=144×2=288
Yield=93%

Step 2: N-(CYANOMETHYL) 2-ACETOXY 4-ACETAMINO 5-CHLOROBENZAMIDE 104 g of triethylamine and 890 cc of chloroform were introduced into a 3 liter balloon flask provided with a sealed agitator, a reflux condenser and a thermometer. The solution obtained was cooled to 5° C. 51 g of amino acetonitrile hydrochloride was then gradually added, with the temperature being maintained at between 5° and 10° C. Thereafer over a period of 30 minutes and at a temperature of between 0° and 5° C., 143 g of 2-acetoxy 4-acetamino 5-chlorobenzoyl chloride in finely divided form was added. A dark-coloured solution resulted, which was agitated, first, for a period of 2 hours at 10° C. and, thereafter, for 2 hours at ambient temperature.

The chloroform was then distilled off; first under vacuum, and, thereafter, by azeotropic distillation with water. The triethylamine hydrochloride dissolved and the nitrile product formed crystallized out. The nitrile product was drained, abundantly washed with water until the chloride ions were removed and then dried at 50° in a ventilated oven.

Weight obtained=143 g
MP=201° C.
Yield=94%

Step 3: N-[(1-ETHYL 2-IMIDAZOLIN-2-YL)METHYL]2-HYDROXY 4-ACETAMINO 5-CHLOROBENZAMIDE 143 g of N-(cyanomethyl) 2-acetoxy 4-acetamino 5-chlorobenzamide was introduced into a one liter balloon flask provided with sealed agitator, a reflux condenser on which there was disposed a bubble a bubble counter containing vaseline oil, a thermometer and a dropping funnel. Thereafer, 123 g of N-ethyl ethylene diamine were rapidly added dropwise. The reaction was exothermic. the temperature rose to 110° C. and the amount of gas evolved was substantial. A thick solution was obtained. The solution was heated to temperature of 120° and then, after 25 minutes of heating, drops of carbon disulphide were added and the temperature was then maintained at 120° for a further period of 20 minutes until the gas ceased to be evolved.

The thick solution obtained was slightly cooled and dissolved in about 200 cc of chloroform. There was formed a very fine precipitate which drained very slowly and which was very difficult to wash. The precipitate was dried in the air.

Weight obtained=76 g
Yield=43%
Mol. wt (HClO$_4$N/10 )=298

The N.M.R. spectrum of the product was compatible with a mixture of 25% of the 4-amino product and 75% of the 4-acetamino product. The calculated molecular weight of that mixture was 291 .

Step 4: N-[1-ETHYL 2-IMIDAZOLIN-2-YL)METHYL]2-HYDROXY 4-AMINO 5-CHLOROBENZAMIDE HYDROCHLORIDE 76 g of N-[(1-ethyl 2-imidazolin-2-yl)methyl]2-hydroxy 4-acetamino 5-chlorobenzamide and 380 cc of methanol containing 25 g of hydrogen chloride gas were introduced into a one liter balloon flask provided with a reflux condenser.

The solution obtained was heated under reflux for 1 hour; was concentrated to a volume of 300 cc and then cooled. The hydrochloride product which crystallized out was drained, washed with methanol and dried at 40°.

Weight product obtained=29 g
Yield=39%

The 29 g hydrochloride product was redissolved hot in 145 cc of methanol. The boiling solution was filtered with carbon black. The product recrystallized very quickly and even partly on the filter. The hydrochloride product which recrystallized out was drained, washed with methanol and dried at 40°.

(1) Weight obtained = 7 g
Mol. wt. (AgNO$_3$N/10) = 336

The NMR spectrum confirmed the presence of a small amount of impurity in the product.

The product was redissolved hot in the recrystallization filtrate and the solution thus obtained was concentrated, filtered and cooled. After draining, washing and drying, 8 g of impure product was recovered. The 8 g was immediately recrystallized from 56 cc of methanol.

(2) Weight obtained = 2.5 g
Mol. wt. (AgNO$_3$N/10) = 338
Total weight (1+2) obtained = 9.5 g
Recrystallization yield = 33%

The NMR spectrum was compatible with the desired product but there remained a slight trace of impurity. Two other recrystallization operations from methanol were necessary to provide a pure product. Finally, recovery of the purified product was effected:
Weight obtained = 6 g
Yield of the recrystallization operations = 21%
Mol. wt. (AgNO$_3$N/10) = 339
Total yield = 8%
MP = 270° C. approximately.

The NMR spectrum was compatible with the structure of the expected product.

EXAMPLE XIII:
N-[1-CYCLOHEXEN-1-YL-METHYL)2-(IMIDAZOLIN-2-YL)METHYL]2-METHOXY 4-AMINO 5-CHLORO BENZAMIDE 38 g of N-(cyanomethyl) 2-methoxy 4-amino 5-chloro benzamide and 54 g of N-(cyclohexen-1-yl-methyl) ethylenediamine were introduced into a 500 cc balloon flask provided with a sealed agitator, a reflux condenser on which there was disposed a bubble counter containing vaseline oil, a thermometer and a dropping funnel. Heating was effected using an oil bath at from 115° to 120° C. 5 drops of carbon disulphide were then added and heating was continued until ammonia was evolved, namely at 130° C. Heating at 135° to 140° C. was maintained throughout the period for which gas was evolved (65 minutes). Then, 3 additional drops of carbon disulphide were added to bring the reaction to an end. The initial suspension was transformed into a chestnut-colored solution.

When the reaction was terminated, cooling to 50° was effected. The product which began to crystallize out was dissolved in a mixture of 50 cc of ether and 25 cc of acetone. The product was recrystallized, drained, washed with ether and dried in the air.
Weight obtained = 42 g
MP = 158° C.
Yield = 70%

The 42 g of product was recrystallized from 65 cc of absolute ethanol. After cooling, the recrystallized product was drained, washed with a cold mixture of ethanol and water (50/50) and dried at 40°.
Weight obtained:
1st stream = 32.5 g MP = 154° C.
2nd stream = 4.5 g MP = 156° C. pale yellow product
Total weight obtained = 37 g
Recrystallization yield = 88%

The 37 g of product was redissolved hot in 148 cc of absolute ethanol. The boiling solution was filtered with carbon black and 111 cc of ethanol was removed by distilling under vacuum without exceeding a temperature of 30°. The residue was dissolved in 37 cc of ice water. The product which crystallized out was drained, washed with ice water and dried at 40° in a ventilated oven.
Weight product obtained = 33 g
Recrystallizaion yield = 89%
MP = 158° C.

32 g of product was dissolved in 96 cc of chloroform. The solution was filtered with carbon black and the solvent was immediately removed by distilling under a slight vacuum. The remaining paste was then dissolved with 85 cc of methyl ethyl ketone. The product which crystallized out was drained, washed with methyl ethyl ketone and dried at 40°.
Weight obtained = 23.5 g
Recrystallization yield = 74%

Finally, 21 g of product was dissolved in 84 cc of chloroform. The solution was filtered with carbon black and the chloroform was removed by distillation under a slight vacuum until a constant weight of product was attained. The remaining solid, after powdering, was poured over a Buchner funnel, washed with ether and dried. The dried powder was then dissolved in water, obtained, washed with water to remove any traces of solvent and again dried at 40° in a ventilated oven.
Weight obtained = 17 g
Mol. wt. (HClO$_4$N/10-potentiometry) = 375
MP = 152°–153° C.
Recrystallization yield = 81%
Yield of the recrystallization operations = 47%
Total yield = 33%

EXAMPLE XIV: N-[1-ETHYL 2-IMADAZOLIN-2-YL)ETHYL]2-METHOXY 4-AMINO 5-CHLOROBENZAMIDE

Step 1: N-(1-CYANOETHYL) 2-METHOXY 4-AMINO 5-CHLOROBENZAMIDE 86.5 g of 2-methoxy 4-amino 5-chlorobenzoic acid in finely divided form, 550 cc of chloroform and 43.5 g of triethylamine were introduced into a two liter balloon flask provided with a sealed agitator, a reflux condenser, a thermometer and a dropping funnel. Heating was effected until all the acid dissolved. Cooling to 0° C. was effected and then 46.5 g of ethyl chloroformate was poured in dropwise, with temperature being maintained at between 0° and 5° C. by cooling in an ice bath.

When the addition operation was concluded, agitation was effected for a period of 1 hour at between 5° and 10° and a solution of 33 g of 2-aminopropionitrile in 99 c of chloroform was added dropwise. The temperature was then allowed to rise to 20° and then heating was effected for 2 hours at 50°.

Water was then added to the resulting solution and the chloroform was entrained and removed. After cooling, the medium was made alkaline in order to dissolve any acid which had not reacted. Then, the precipitate which had formed was drained, washed with water until the $^-$ ions were removed and dried at 50°.

Weight obtained = 80 g

Yield 73.5%

The 80 g of substance recovered was recrystallized from 320 cc of 2-ethoxy ethanol.

Weight obtained = 43 g
MP = 220° C.
Recrystallization yield = 54%
Total yield = 39.5%

Step 2: N-[1-(ETHYL 2-IMIDAZOLIN-2-YL)ETHYL]2-METHOXY 4-AMINO 5-CHLOROBENZAMIDE 43 g N-(1-cyanoethyl) 2-methoxy 4-amino 5-chloro benzamide in finely divided form and 30 g pf N-ethyl ethylenediamine were introduced into a 250 cc balloon flask provided with a sealed agitator, a reflux condenser on which there was disposed a bubble counter containing vaseline oil, a thermometer and a dropping funnel. The suspension thus produced was heated on an oil bath to a temperature pf 110°. 10 drops of carbon disulphide were then added. White fumes were immediately formed: ammonia was evolved and the medium gradually solubilized in order to finally provide a thick solution.

Heating was maintained for 1 hour until the gas ceased to be evolved. After cooling, a product crystallized out.

It was dissolved with ether, drained, washed with ether, dried in the air and then at 50°.

Weight obtained = 50 g
MP = 162° C.
Yield 91%

The 50 g of product was redissolved hot in 200 cc of acetonitrile. After cooling, the product crystallized out very quickly. It was drained, washed with acetonitrile and dried at 50°.

Weight of product obtained = 42.5 g
Recrystallization yield = 85%

The 42.5 g of product was redissolved in about 180 cc of chloroform. The solution was filtered with carbon black and concentrated under vacuum until the chloroform was totally removed. The residue was dissolved with ether. The product which recrystallized out was drained, washed with ether and dried in the air at 50°.

Weight obtained = 39 g
MP = 180° C.
Mol. wt. (H$_2$SO$_4$N/10-potentiometry) = 327
Purification yield = 91 %
Yield of the purification operations = 77%
Total yield = 70%

EXAMPLE XV:

N-[1-ETHYL 4,5-DIMETHYL 2-(IMIDAZOLIN-2-YL)METHYL]2-METHOXY 4-AMINO 5-CHLOROBENZAMIDE 39 g of N-(cyanomethyl) 2-methoxy 4-amino 5-chloro benzamide in finely divided form and 38 g of N-ethyl 2,3-butane diamine were introduced into a 500 cc balloon flask provided with a sealed agitator, a reflux condenser on which there was disposed a bubble counter containing vaseline oil, a thermometer and a dropping funnel. The thick suspension obtained was heated using an oil bath at a temperature of 130° C. 6 drops of carbon disulphide were then added. Gas immediately began to be evolved and the medium gradually became more fluid. After heating for 1 hour, 1 drop of carbon disulphide was added and then a further drop was added 1 hour afterwards.

By that time, the initial suspension was transformed into a thick chestnut-coloured solution. Heating was continued for 3 hours more, until the gas ceased to be evolved. The reaction mixture was then cooled and a product which was half crystallized was obtained. The product was dissolved in ether, drained, washed with ether, dried in the air and then under vacuum in a desiccator.

Weight of product obtained = 56 g
Theoretical amount = 55 g

The 56 g of product was redissolved in 160 cc of dried chloroform. The solution obtained was filtered with carbon black and then the chloroform was distilled off, terminating under vacuum, until a constant weight of product was achieved. The residue was dissolved with ether and crystallized slowly. The crystals obtained were drained, washed with ether and then dried in the air.

Weight obtained = 56 g
MP = about 130° C.

The product was redissolved in 250 cc of water and 10 cc of concentrated hydrochloric acid. The solution obtained was filtered with carbon black and then cooled in an ice-salt bath. It was then poured into a separating funnel. 250 cc of cold chloroform was added, followed by 24 cc of 20% ammonia (phenolphthalein turns pale pink).

The product which precipitated immediately passed into the chloroform. After the organic phase settle, the aqueous solution was again extracted twice with chloroform. The combined chloroform phases were dried over sodium sulphate, then over a molecular sieve and finally filtered with carbon black. The chloroform was distilled, terminating under vacuum, until a constant weight of product was attained. The residue which was dissolved with ether and crystallized immediately. The crystals obtained were drained, washed with ether and dried in the air.

Weight obtained = 31 g
MP = about 144° C.
Yield = 56%

The 31 g of product was redissolved in 200 cc of boiling acetone. A solution of 3.35 g of hydrogen chloride gas in 20 cc of acetone was then added. The hydrochloride which formed precipitated immediately in the form of a paste. The product obtained was drained, washed with acetone and dried. Weight obtained = 35 g. The NMR spectrum was compatible with the expected structure, but with a half mole of water.

Yield to hydrated product = 100%

The 35 g of hydrochloride was redissolved in 300 cc of water. The solution obtained was filtered three times with carbon black and then made alkaline with 20% ammonia.

Product recovered:
Weight obtained = 22 g
MP = 152°-154° C.
Purification yield = 71%
Total yield = 40%

Pharmaceutical Composition

The compounds of the invention can be administered in any number of conventional forms such as capsules, tablets, pills, in granulated form or as an injectable solution. Many methods for compounding these preparations are well-known to the art. Substances which are inert relative to the compounds of the invention can be used in these preparations, such as lactose, magnesium stearate, starch, talc, cellulose, levilite, alkali metal lauryl-sulphates, saccharose and other vehicles commonly employed in pharmaceutical preparations.

The compounds may be administered in doses of about 50–750 mg per day taken in 1 or more stages.

The examples which follow illustrate several pharmaceutical preparations, each made in a conventional manner from the compounds of the invention.

EXAMPLE XVI—tablets

| | |
|---|---|
| N—[(1-ethyl 2-imidazolin-2-yl)methyl] 2-methoxy 4-amino 5-chlorobenzamide | 100 mg |
| dried starch | 20 mg |
| lactose | 100 mg |
| methylcellulose 1500 cps | 1.5 mg |
| levilite | 10 mg |
| magnesium stearate | 4 mg |
| for 1 tablet. | |

EXAMPLE XVII—capsules

| | |
|---|---|
| N—[(1-allyl 2-imidazolin-2-yl)methyl] 2-methoxy 4-amino 5-chlorobenzamide | 50 mg |
| microcrystalline cellulose | 50 mg |
| methylcellulose 1500 cps | 1 mg |
| magnesium stearate | 5 mg |
| talc | 2 mg |
| for 1 capsule. | |

EXAMPLE XVIII—injectable solution

| | |
|---|---|
| N—[(1-ethyl 2-imidazolin-2-yl)methyl] 2-allyloxy 4-amino 5-chlorobenzamide | 40 mg |
| 1N hydrochloric acid | 0.1 ml |
| sodium chloride | 14 mg |
| for 2 ml. | |

EXAMPLE XIX—injectable solution

| | |
|---|---|
| N—[(1-ethyl 2-imidazolin-2-yl)methyl] 2-methoxy 4-amino 5-bromobenzamide | 100 ml |
| 1N hydrochloric acid | 0.250 ml |
| sodium chloride | 8 mg |
| for 2 ml | |

To prepare the tablets, the selected compound is mixed with the starch and lactose by the method of successive dilutions; the mixture is granulated with methylcellulose. The levilite, magnesium stearate and talc are added to the granules before proceeding with compression.

It is possible to replace the methylcellulose with any other appropriate granulating agent, such as ethylcellulose, polyvinylpyrrolidone or starch paste. The magnesium stearate may be replaced by stearic acid.

When preparing injectable solutions, it is possible to dissolve the compound of the invention in the following acids: hydrochloric or levulinic acid, gluconic acid, or glucoheptonic acid. The solution is prepared under sterile conditions and made isotonic with an alkali metal chloride such as sodium chloride, then preservations are added. It is also possible to prepare the same solution without adding any preservatives; the ampoule is then filled under nitrogen and sterilized for ½ hour at 100° C.

The inventive benzamides were subjected to toxicological and pharmacological evaluations.

The compounds according to the invention were the subject of a toxicological study to determine the lethal doses ($LD_{50}$) in male mice, the compounds being administered intravenously. Metoclopramide was employed as a standard. The compounds of Examples X–XIV (1–14) were tested. Table (I) sets out the values with respect to said ($LD_{50}$) tests.

TABLE (I)

| Example | $LD_{50}$ in mg/kg (base) intravenously |
|---|---|
| 1 | 27.1–27.2 |
| 2 | 31.8 |
| 3 | 47.8–48.5 |
| 4 | 28–27.4 |
| 5 | 25.5–26.1 |
| 6 | 25.5–24.4 |
| 7 | 23.4–24.4 |
| 8 | 45.1–39.9 |
| 9 | 31.3–29 |
| 10 | 38.4–41.9 |
| 11 | 30.4 |
| 12 | 59.3 |
| 13 | 61.6 |
| 14 | 14.6 |
| METOCLOPRAMIDE | 37.9 |

A pharmacological study was conducted to evaluate the gastromotor effect of the compounds of the invention. The method used consisted of measuring the amount of a standard meal evacuated by rats, 60 minutes after administration thereof. The rats received the compound to be studied intraperitoneally 30 minutes before the meal, using the procedure described by DROPLEMAN et al in J. Pharm. Meth. 1980, Vol. 4, pp. 227–230, in three different doses (1, 3 and 9 mg/kg).

The results of the study are recorded in Table (II). The activity of the compounds according to the invention are compared to that of Metoclopramide, which was taken as the reference compound. Compounds 1 to 14 are, respectively, the compounds formed in Examples I–XIV.

TABLE (II)

| | | Gastric Emptying | |
|---|---|---|---|
| Compound | Dose in mg/kg (IP) (base) | Weight of meal remaining in the stomach (mg) | % variation |
| 1 | — | 1816 ± 47 | — |
| | 1 | 1690 ± 43 | +7 |
| | 3 | 1346 ± 26 | +26 |
| | 9 | 1202 ± 47 | +34 |
| 2 | — | 1854 ± 87 | — |
| | 1 | 1709 ± 60 | +8 |
| | 3 | 1461 ± 66 | +21 |
| | 9 | 1169 ± 103 | +37 |
| 4 | — | 1765 ± 118 | — |
| | 1 | 1865 ± 95 | −6 |
| | 3 | 1648 ± 115 | +7 |
| | 9 | 1482 ± 128 | +16 |
| 5 | — | 1879 ± 122 | — |
| | 1 | 1716 ± 72 | +9 |
| | 3 | 1639 ± 107 | +13 |
| | 9 | 1350 ± 122 | +28 |
| 6 | — | 1849 ± 54 | — |
| | 1 | 1543 ± 73 | +17 |
| | 3 | 1312 ± 43 | +29 |
| | 9 | 1033 ± 48 | +44 |
| 7 | — | 1891 ± 87 | — |
| | 1 | 1619 ± 68 | +14 |
| | 3 | 1566 ± 79 | +17 |
| | 9 | 1566 ± 60 | +18 |
| 8 | — | 2061 ± 74 | — |
| | 1 | 1764 ± 99 | +14 |
| | 3 | 1525 ± 111 | +26 |
| | 9 | 1325 ± 84 | +36 |

TABLE (II)-continued

| | Gastric Emptying | | |
|---|---|---|---|
| Compound | Dose in mg/kg (IP) (base) | Weight of meal remaining in the stomach (mg) | % variation |
| 9 | — | 2125 ± 122 | — |
| | 1 | 1635 ± 71 | +23 |
| | 3 | 1432 ± 46 | +33 |
| | 9 | 1355 ± 71 | +36 |
| 10 | — | 1680 ± 86 | — |
| | 1 | 1502 ± 130 | +11 |
| | 3 | 1259 ± 71 | +25 |
| | 9 | 1413 ± 55 | +16 |
| 14 | — | 1817 ± 98 | — |
| | 1 | 1654 ± 77 | +9 |
| | 3 | 1453 ± 69 | +20 |
| | 9 | 1317 ± 141 | +28 |
| METOCLO-PARAMIDE | — | 2230 ± 65 | — |
| | 1 | 1645 ± 74 | +26 |
| | 3 | 1342 ± 48 | +40 |
| | 9 | 1232 ± 28 | +45 |

Another pharmacological study was conducted to determine the central antidopaminergic effects of the compounds of the invention, by evaluating the power of their antagonistic effect in regard to the stereotyped movements induced by apomorphine in two different doses (1.25 mg/kg/IV and 0.5 mg/kg/SC) in rats. The tests were conducted according to conventional procedures.

Table (III) indicates that the compounds of the invention have only a negligible antagonism whereas, when studied under the same conditions, Metoclopramide exhibited a marked stereotypy inhibitor capacity.

TABLE (III)

| Stereotypies In Regard To Apomorphine In Rats | | |
|---|---|---|
| Example | Subcutaneous (S.C.) | Intraperitoneal (I.P) |
| 1 | inactive at 200 mg/kg | inactive at 50 mg/kg |
| 3 | inactive at 200 mg/kg | 19% inhibitor effect at 64 mg/kg |
| 4 | inactive at 100 mg/kg | 26% inhibitor effect at 32 mg/kg |
| 5 | inactive at 200 mg/kg | 8% inhibitor effect at 32 mg/kg |
| 6 | inactive at 200 mg/kg | 20% inhibitor effect at 32 mg/kg |
| 7 | inactive at 200 mg/kg | inactive at 64 mg/kg |
| 8 | inactive at 200 mg/kg | 8% inhibitor effect at 64 mg/kg |
| 9 | inactive at 100 mg/kg | 5% inhibitor effect at 64 mg/kg |
| 10 | inactive at 100 mg/kg | 4% inhibitor effect at 64 mg/kg |
| 11 | inactive at 200 mg/kg | inactive at 64 mg/kg at 64 mg/kg |
| 12 | inactive at 200 mg/kg | 2% inhibitor effect at 54 mg/kg |
| 13 | inactive at 200 mg/kg | 18% inhibitor effect at 64 mg/kg |
| 14 | inactive at 80 mg/kg | inactive at 40 mg/kg |
| METACLOPRAMIDE | $ID_{50}$ = 15-15.2 mg//kg | $ID_{50}$ = 2-2.6 mg//kg |

Another demonstration of a central nervous system (CNS) effect of the compounds of the invention, which was different from that of Metoclopramide, was illustrated by evaluating the cataleptigenic power of the inventive compounds, which was found to be virtually zero, as indicated by Table (IV):

TABLE (IV)

| Example | Cataleptic Activity (Subcutaneous) |
|---|---|
| 1 | inactive at 200 mg/kg |

TABLE (IV)-continued

| Example | Cataleptic Activity (Subcutaneous) |
|---|---|
| 2 | inactive at 200 mg/kg |
| 3 | inactive at 200 mg/kg |
| 4 | inactive at 200 mg/kg |
| 5 | inactive at 200 mg/kg |
| 6 | inactive at 100 mg/kg |
| 7 | inactive at 200 mg/kg |
| 8 | inactive at 200 mg/kg |
| 9 | inactive at 200 mg/kg |
| 10 | inactive at 200 mg/kg |
| 11 | inactive at 200 mg/kg |
| 12 | inactive at 200 mg/kg |
| 13 | inactive at 200 mg/kg |
| 14 | inactive at 80 mg/kg |
| METOCLOPRAMIDE | $ED_{50}$ SC = 30-38 mg/kg |

The cataleptic power of the compounds was determined employing conventional procedures well known to the art.

The absence or virtual absence of side-effects therefore permits use of the compounds of the invention for their therapeutic gastromotor properties with an enhanced level of safety. This invention is not to be limited except as set forth in the following claims.

What is claimed is:

1. Benzamide compounds and pharmacologically acceptable salts thereof of the following general formula (I):

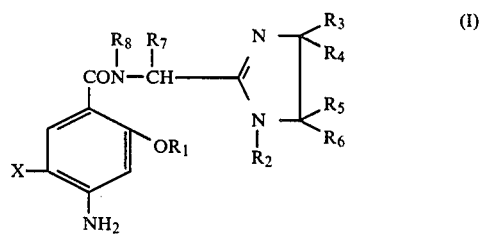

in which:

$R_1$ is a $C_1-C_3$ alkyl, a $C_2-C_3$ alkenyl or a hydrogen atom;

$R_2$ is a $C_1-C_3$ alkyl, $C_2-C_3$ alkenyl, benzyl, $C_3-C_8$ cycloalkyl $C_1-C_3$ alkyl, $C_5-C_8$ cycloalkenyl $C_1-C_3$ alkyl or a hydrogen atom;

$R_3$, $R_4$, $R_5$, $R_6$ $R_7$ and $R_8$ each are a $C_1-C_3$ alkyl or a hydrogen atom; and X is a halogen atom.

2. A benzamide according to claim 1, said benzamide being N-[(1-ethyl 2-imidazolin-2-yl)methyl] 2-methoxy 4-amino 5-chlorobenzamide.

3. A benzamide according to claim 1, said benzamide being N-[(1-allyl 2-imidazolin-2-yl) methyl]2-methoxy 4-amino 5-chlorobenzamide.

4. A benzamide according to claim 1, said benzamide being N-[(1-ethyl 2-imidazolin-2-yl) methyl] 2-allyloxy 4-amino 5-chlorobenzamide.

5. A benzamide according to claim 1, said benzamide being N-[(1-ethyl 2-imidazolin-2-yl) methyl] 2-methoxy 4-amino 5-bromobenzamide.

6. A benzamide according to claim 1, said benzamide being N-methyl, N-[(1-ethyl 2-imidazolin-2-yl) methyl] 2-methoxy 4-amino 5-chlorobenzamide methane sulphonate.

7. A benzamide according to claim 1, said benzamide being N-[(1-methyl 2-imidazolin-2-yl) methyl] 2-methoxy 4-amino 5-chlorobenzamide hydrochloride.

8. A benzamide according to claim 1, said benzamide being N-[(1-ethyl 4-methyl 2-imidazolin-2-yl) methyl] 2-methoxy 4-amino 5-chlorobenzamide.

9. A benzamide according to claim 1, said benzamide being N-[1-(1-ethyl 2-imidazolin-2-yl) ethyl] 2-methoxy 4-amino 5-chlorobenzamide.

10. A pharmaceutical composition for treating patients subject to digestive disorders comprising (a) a therapeutically effective amount of a benzamide compound or a pharmacologically acceptable salt thereof according to claim 1 as active ingredient and (b) a pharmaceutically acceptable excipient.

* * * * *

UNITED STATES PATENT AND TRADEMARK OFFICE
CERTIFICATE OF CORRECTION

PATENT NO. : 4,703,055

DATED : October 27, 1987

INVENTOR(S) : JACQUELINE FRANCESCHINI, ET AL.

It is certified that error appears in the above-identified patent and that said Letters Patent is hereby corrected as shown below:

AT [56] IN THE REFERENCES

"Ried, W., Earl, H. Chem Ber. 115, 475-482 (1982)." should read --Ried, W., Erle, H.-E., Chem Ber. 115, 475-482 (1982).--.

COLUMN 1

Line 6, close up left and right margins.
Line 26, "loalkyl" should read --cloalkyl--.
Line 27, "Cycloalkenyl" should read --cycloalkenyl--.

COLUMN 2

Line 14, "following formula" should read --following general formula--.
Line 42, delete "is".

UNITED STATES PATENT AND TRADEMARK OFFICE
CERTIFICATE OF CORRECTION

PATENT NO. : 4,703,055

DATED : October 27, 1987

INVENTOR(S) : JACQUELINE FRANCESCHINI, ET AL.

It is certified that error appears in the above-identified patent and that said Letters Patent is hereby corrected as shown below:

COLUMN 2 (continued)

Lines 41-47, " 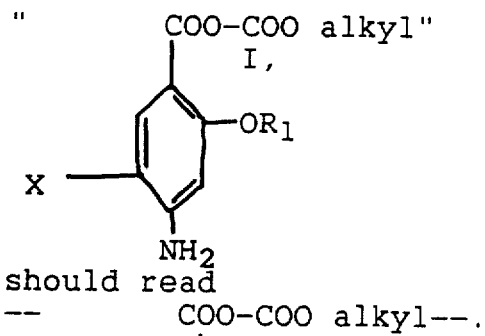 I, should read

-- 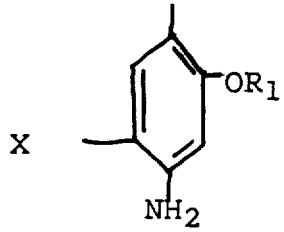 COO-COO alkyl --.

COLUMN 3

Line 10, "into" should read --Into--.
Line 33, "additin" should read --addition--.
Line 39, "N-[1-ETHYL 2-IMIDAZOLIN-2 YL)" should read --N-[(1-ETHYL 2-IMIDAZOLIN-2 YL)--.
Line 65, "occured." should read --occurred.--.

UNITED STATES PATENT AND TRADEMARK OFFICE
CERTIFICATE OF CORRECTION

PATENT NO. : 4,703,055

DATED : October 27, 1987

INVENTOR(S) : JACQUELINE FRANCESCHINI, ET AL.

It is certified that error appears in the above-identified patent and that said Letters Patent is hereby corrected as shown below:

COLUMN 4

Line 13, "containg" should read --containing--.
Line 46, "EXAPLE III" should read --EXAMPLE III:--.
Line 66, "evolving," should read --evolving--.

COLUMN 5

Line 8, "were" should read --was--.
Line 21, "coloured" should read --colored--.
Line 62, "EXAMPLE IV" should read --EXAMPLE IV:--.
Line 65, "4-AMINO 5-CHLOROBENZAMIDE)" should read --4-AMINO 5-CHLOROBENZAMIDE--.

COLUMN 6

Line 45, "EXAMPLE V" should read --EXAMPLE V:--.

COLUMN 7

Line 1, "were" should read --was--.
Lines 57-58, "N-(CYANOMETHYL 2-ALLYLOXY 4-AMINO 5-CHLORO BENZAMIDE" should read --N-(CYANOMETHYL) 2-ALLYLOXY 4-AMINO 5-CHLOROBENZAMIDE"--.

UNITED STATES PATENT AND TRADEMARK OFFICE
CERTIFICATE OF CORRECTION

PATENT NO. : 4,703,055

DATED : October 27, 1987

INVENTOR(S) : JACQUELINE FRANCESCHINI, ET AL.

It is certified that error appears in the above-identified patent and that said Letters Patent is hereby corrected as shown below:

COLUMN 8

Line 10, "dissoled" should read --dissolved--.
    Line 31, "vapours" should read --vapors--.
    Line 54, "Weight obtained=31" should read --Weight obtained=31 g--.

COLUMN 9

Line 28, "0° 5°." should read --0° and 5°.--.
    Line 38, "the" should read --then--.
    Line 44, "poduct" should read --product--.
    Line 57, "is" should read --in--.

COLUMN 10

Line 14, "ai" should read --air--.
    Line 34, "2METHOXY 4-AMINO 5CHLOROBENZAMIDE" should read --2-METHOXY 4-AMINO 5-CHLOROBENZAMIDE--.
    Line 41, "dissoluiton" should read --dissolution--.

COLUMN 11

Line 10, "2methoxy" should read --2-methoxy--.
    Line 11, "5-chloro benzamide" should read --5-chlorobenzamide--.
    Line 52, "phosphate." should read --sulphate.--.
    Line 61, "SULFONATE" should read --SULPHONATE--.

UNITED STATES PATENT AND TRADEMARK OFFICE
CERTIFICATE OF CORRECTION

PATENT NO. : 4,703,055

DATED : October 27, 1987

INVENTOR(S) : JACQUELINE FRANCESCHINI, ET AL.

It is certified that error appears in the above-identified patent and that said Letters Patent is hereby corrected as shown below:

COLUMN 12

Line 3, "sulphonte" should read --sulphonate--.
Line 42, "dissoled." should read --dissolved.--.
Line 60, "4-AMINO 5CHLOROBENZAMIDE" should read
--4-AMINO 5-CHLOROBENZAMIDE--.

COLUMN 13

Line 14, "N-[(1-ETHYL 4-METHYL 2-IMIDAZOLIN-2-YL" should
read --N-[(1-ETHYL 4-METHYL 2-IMIDAZOLIN-2-YL)--.

COLUMN 14

Line 32, "40" should read --40°.--.
Line 33, delete ".".
Line 46, "(HClO$_4$N/10)" should read --(HClO$_4$N/10)--.

COLUMN 15

Line 1, "until thick" should read --until a thick--.
Line 7, "were" should read --was--.
Line 51, "5chlorobenzoic" should read --5-chlorobenzoic--.

COLUMN 16

Line 5, "Thereafer" should read --Thereafter--.
Line 8, "dark-coloured" should read --dark-colored--.
Line 29, delete "a bubble" (second occurrence).
Line 31, "Thereafer," should read --Thereafter,--.

UNITED STATES PATENT AND TRADEMARK OFFICE
CERTIFICATE OF CORRECTION

PATENT NO. : 4,703,055

DATED : October 27, 1987

INVENTOR(S) : JACQUELINE FRANCESCHINI, ET AL.

Page 6 of 8

It is certified that error appears in the above-identified patent and that said Letters Patent is hereby corrected as shown below:

COLUMN 16 (continued)

Line 32, "were" should read --was--.
Line 33, "the" (first occurrence) should read --The--.
Line 35, "to temperature" should read --to a temperature--.
Line 36, "heating, drops" should read --heating, 5 drops--.
Line 52, "291 ." should read --291.--.
Line 53, "N-[1-ETHYL" should read --N-[(1-ETHYL--.
Line 56, "HYDROCHLORIDE 76 g of N-[(1-ethyl" should read --HYDROCHLORIDE ¶ 76 g of N-[(1-ethyl--.
Line 61, close up left and right margin.
Line 64, close up left margin and "at" should read --at 40°.--.
Line 65, delete "40°".

COLUMN 17

Line 34, "N-[1-CYCLOHEXEN-1-YL-METHYL)2-" should read --N-[(1-CYCLOHEXEN-1-YL-METHYL)2---.
Line 36, "4-AMINO 5-CHLORO BENZAMIDE" should read --4-AMINO 5-CHLOROBENZAMIDE--.
Line 48, "throughtout" should read --throughout--.

COLUMN 18

Line 29, "obtained," should read --drained,--.
Line 39, "EXAMPLE XIV: N-[1-ETHYL" should read --EXAMPLE XIV: ¶ N-[(1-ETHYL--.
Line 40, "2-IMADAZOLIN-2-YL)ETHYL]2-METHOXY" should read --2-IMIDAZOLIN-2-YL)ETHYL]2-METHOXY--.

UNITED STATES PATENT AND TRADEMARK OFFICE
CERTIFICATE OF CORRECTION

PATENT NO. : 4,703,055

DATED : October 27, 1987

INVENTOR(S) : JACQUELINE FRANCESCHINI, ET AL.

It is certified that error appears in the above-identified patent and that said Letters Patent is hereby corrected as shown below:

COLUMN 18 (continued)

Line 57, "99 c" should read --99 cc--.
    Line 65, "until the" should read --until the $Cl^-$ ions were removed and dried at 50°.--.
    Line 67, delete "- ions were removed and dried at 50°.".

COLUMN 19

Line 1, "Yield 73.5%" should read --Yield=73.5%--.
    Line 13, "pf" should read --of--.
    Line 19, "pf" should read --of--.
    Line 31, "Yield 91%" should read --Yield=91%--.

COLUMN 20

Line 2, "chestnut-coloured" should read --chestnut-colored--.
    Line 29, "settle," should read --settled,--.

COLUMN 21

Line 43, "100 ml" should read --100 mg--.
    Line 63, "preservations" should read --preservatives--.

COLUMN 22

Line 6, "X-XIV" should read --I-XIV--.

UNITED STATES PATENT AND TRADEMARK OFFICE
CERTIFICATE OF CORRECTION

PATENT NO. : 4,703,055

DATED : October 27, 1987

INVENTOR(S) : JACQUELINE FRANCESCHINI, ET AL.

It is certified that error appears in the above-identified patent and that said Letters Patent is hereby corrected as shown below:

COLUMN 23

Line 50, delete "at 64 mg/kg".

COLUMN 24

Line 47, "cycloalkyl$C_1$-$C_3$ alkyl, $C_5$-$C_8$ cyloalkenyl $C_1$-$C_3$" should read --cycloalkyl-$C_1$-$C_3$ alkyl, $C_5$-$C_8$ cycloalkenyl-$C_1$-$C_3$--.

Line 49, "$R_6$ $R_7$" should read --$R_6$, $R_7$--.

Signed and Sealed this

Seventh Day of June, 1988

Attest:

DONALD J. QUIGG

Attesting Officer      Commissioner of Patents and Trademarks